United States Patent
Ouellet et al.

(10) Patent No.: US 10,533,320 B2
(45) Date of Patent: Jan. 14, 2020

(54) REINFORCEMENT FOR A CONCRETE TILE

(71) Applicant: LE SQUAREDECKO INC., Sherbrooke (CA)

(72) Inventors: André Ouellet, Sherbrooke (CA); Vincent Houle, Sherbrooke (CA)

(73) Assignee: LE SQUAREDECKO INC., Sherbrooke, QC (CA)

(*) Notice: Subject to any disclaimer, the term of this patent is extended or adjusted under 35 U.S.C. 154(b) by 0 days.

(21) Appl. No.: 15/470,212

(22) Filed: Mar. 27, 2017

(65) Prior Publication Data

US 2017/0254079 A1    Sep. 7, 2017

Related U.S. Application Data

(63) Continuation-in-part of application No. 14/428,028, filed as application No. PCT/CA2013/000778 on Sep. 13, 2013, now abandoned.

(60) Provisional application No. 61/700,909, filed on Sep. 14, 2012.

(51) Int. Cl.
| | |
|---|---|
| *E04C 2/06* | (2006.01) |
| *E04C 2/04* | (2006.01) |
| *G01N 3/02* | (2006.01) |
| *G01N 33/38* | (2006.01) |
| *E04B 5/12* | (2006.01) |
| *E04C 2/28* | (2006.01) |

(52) U.S. Cl.
CPC ................ *E04C 2/06* (2013.01); *G01N 3/02* (2013.01); *G01N 33/383* (2013.01); *E04B 5/12* (2013.01); *E04C 2/04* (2013.01); *E04C 2/28* (2013.01); *E04C 2002/046* (2013.01)

(58) Field of Classification Search
CPC ... E04C 2/06; E04C 2/04; E04C 2/044; E04C 2002/046; E04C 2/08; E04C 3/04; E04C 3/20; E04C 2/28; E04C 2/50; E04B 5/12; G01N 3/02; G01N 33/383
See application file for complete search history.

(56) References Cited

U.S. PATENT DOCUMENTS

| 15,221 | A | * | 7/1856 | Clow | E04C 3/292 |
| | | | | | 52/649.6 |
| 826,042 | A | * | 1/1906 | Loveley | E04C 3/292 |
| | | | | | 52/127.3 |
| 1,073,931 | A | * | 9/1913 | Royse | E04C 3/292 |
| | | | | | 52/649.6 |
| 1,094,841 | A | * | 4/1914 | Ellinger | E04B 1/185 |
| | | | | | 52/649.6 |

(Continued)

OTHER PUBLICATIONS

PCT/CA2013/000778 International search report.
PCT/CA2013/000778 IPRP.

*Primary Examiner* — Phi D A
(74) *Attorney, Agent, or Firm* — Anglehart et al.

(57) ABSTRACT

A reinforced concrete tile having top and bottom surfaces defining a thickness, the reinforced concrete tile comprising two or more reinforcing inserts imbedded in the concrete tile in proximity to the bottom surface, the two or more reinforcing inserts being of elongated shape and comprising a plurality of scales distributed along the length and extending upwardly from the bottom surface whereby a compensating force is created upon application of a load on the top surface such that deflection is reduced as the load is increased for at least a range of loads until a yield load is reached.

7 Claims, 7 Drawing Sheets

(56) References Cited

U.S. PATENT DOCUMENTS

| | | | |
|---|---|---|---|
| 2,210,444 A | 8/1940 | Case | |
| 3,529,918 A * | 9/1970 | Jureit | E04B 1/49 403/384 |
| 4,115,049 A * | 9/1978 | Grubb | B28B 17/0018 249/121 |
| 4,305,239 A * | 12/1981 | Geraghty | E04B 1/41 52/379 |
| 4,370,840 A * | 2/1983 | Bisbee | F27D 1/144 403/393 |
| 4,454,699 A * | 6/1984 | Strobl | F16B 21/082 403/298 |
| 4,753,559 A * | 6/1988 | Pentesco | B21D 35/00 405/259.3 |
| 4,963,051 A * | 10/1990 | Hutter | F16B 2/18 403/298 |
| 5,024,039 A | 6/1991 | Karhumaki | |
| 5,259,161 A * | 11/1993 | Carter | E04C 5/06 52/127.3 |
| 6,276,644 B1 * | 8/2001 | Jennings | F16L 3/04 248/49 |
| 6,360,505 B1 * | 3/2002 | Johns | E04F 13/147 249/15 |
| 7,108,453 B2 | 9/2006 | Harris | |
| 8,051,619 B2 * | 11/2011 | Hohmann, Jr. | E04G 21/1883 52/677 |
| 8,931,993 B2 * | 1/2015 | Komsitsky | B64C 1/403 411/450 |
| 2007/0147975 A1 * | 6/2007 | Homner | F16B 5/0642 411/510 |
| 2009/0120030 A1 | 5/2009 | Garza | |
| 2013/0279978 A1 * | 10/2013 | Sippola | A61H 3/066 404/40 |
| 2015/0233066 A1 * | 8/2015 | Ouellet | E01C 11/18 428/209 |

\* cited by examiner

REINFORCEMENT FOR A CONCRETE TILE

This application is a continuation-in-part of U.S. patent application Ser. No. 14/428,028 filed Mar. 13, 2015, now pending, that is a national stage of PCT/CA2013/000778 filed Sep. 13, 2013, now abandoned, that claims priority of U.S. provisional patent application 61/700,090 filed Sep. 14, 2012.

FIELD OF THE INVENTION

The present invention relates generally to concrete elements but more particularly to a reinforcement for a concrete tile.

BACKGROUND OF THE INVENTION

Concrete tiles used as a decorative element for pavement, patios, walkways, etc are quite popular. Typically, no steel reinforcement are within the concrete as the products are placed directly on the ground. Sometimes, when they need to put concrete over a structure, manufacturer will decide to increase thickness of the product or, they use a steel reinforcement grid placed within. Generally midway or the lower third of the thickness of the concrete. There is also a technique known as ferro-cement which combines steel rebars with metal mesh such as chicken wire mesh in order to create a stronger concrete. Typically, whether in the case of reinforced concrete or ferro-cement, careful positioning of the steel armature as well as ensuring that the armature does not move during the compacting and vibrating of the concrete makes the process rather difficult to achieve in an optimal way and only highly trained and skilled artisans can produce a consistently good piece of decorative concrete.

SUMMARY OF THE INVENTION

In view of the foregoing disadvantages inherent in the known devices now present in the prior art, the present invention, which will be described subsequently in greater detail, isto provide objects and advantages which are:

In one aspect of the invention there is provided a reinforced concrete tile having top and bottom surfaces defining a thickness, the reinforced concrete tile comprising two or more reinforcing inserts imbedded in the concrete tile in proximity to the bottom surface, the two or more reinforcing inserts being of elongated shape and comprising a plurality of scales distributed along the length and extending upwardly from the bottom surface whereby a compensating force is created upon application of a load on the top surface such that deflection is reduced as the load is increased for at least a range of loads until a yield load is reached.

In another aspect there is provided a method for manufacturing a reinforced concrete tile comprising providing a mold for shaping the tile having a top and bottom surface; positioning in the mold two or more reinforcing inserts to be imbedded in the concrete tile in proximity to the bottom surface, the two or more reinforcing inserts being of elongated shape and comprising a plurality of scales distributed along the length and extending upwardly from the bottom surface; pouring unset concrete in the mold; permitting the concrete to set; and testing the tile to obtain a load-deflection curve and wherein for a reinforced tile deflection is reduced as the load is increased for at least a range of loads until a yield load is reached To provide for a way to install a reinforcement for a concrete tile which is easy to position while providing an excellent means of reinforcement.

In order to do so, in one aspect the invention consists of a reinforcement for concrete tiles comprising an element formed in a flat elongated shape having a top and bottom surface, a plurality of scales extending from the top surface at an angle thereto, and wherein the angle of a number of the scales are formed in an opposite direction from the remaining scales, and adapted such that when in place within a concrete tile the element cannot slip out therefrom, and adapted such that when the tile experiences a bending force the element creates a compressive force opposite the bending force to thereby prevent the tile from bending and breaking.

The reinforcement has its scales; scales are formed in two parallel rows in a direction along the elongated length of the element.

The number of the scales that are formed in the opposite direction is half of the total of the plurality of scales.

In one aspect the elongated shape of the element is rectangular.

The element and the plurality of scales are formed from a material chosen from a list of materials comprising non-corroding metals, polymers, and composites. Preferably, the plurality of scales is formed from galvanized steel.

An apparatus for making an improved reinforced concrete tile formed from concrete and including at least one reinforcing element placed within an interior section thereof that is formed in a flat elongated shape having a top and bottom surface, a plurality of scales extending from the top surface at an angle thereto, and wherein the angle of a number of the scales are formed in an opposite direction from the remaining scales, wherein the apparatus for making the reinforced concrete tile comprises a sub-structure includes a pair of straight beams adapted to be placed in a spaced and parallel configuration from one another a distance adapted to hold a chosen mold member thereon. A mold member having a bottom surface and four walls forming a volume and shape chosen to form the concrete tile, and including a plurality of peg members placed within the volume of the mold member such that the at least one reinforcing element is held in a chosen position, and adapted such that when concrete is poured into the mold member the at least one reinforcing element does not move, and when the concrete is set the at least one reinforcing element is in desired permanent positions.

In one aspect there is provided a reinforced concrete tile having top and bottom surfaces defining a thickness, the reinforced concrete tile comprising two or more reinforcing elements imbedded in the concrete tile in proximity to the bottom surface, the two or more reinforcing inserts being of elongated shape and spanning a length of the tile in a direction substantially perpendicular to a width of the tile, the reinforcing inserts comprising a plurality of scales distributed along the length and extending upwardly from the bottom surface to a depth of between 20 to 80% of the thickness and having a width of about 1 to 25% of the width.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter which contains illustrated preferred embodiments of the invention.

DETAILED DESCRIPTION OF THE PREFERRED EMBODIMENT

Figure 1A:
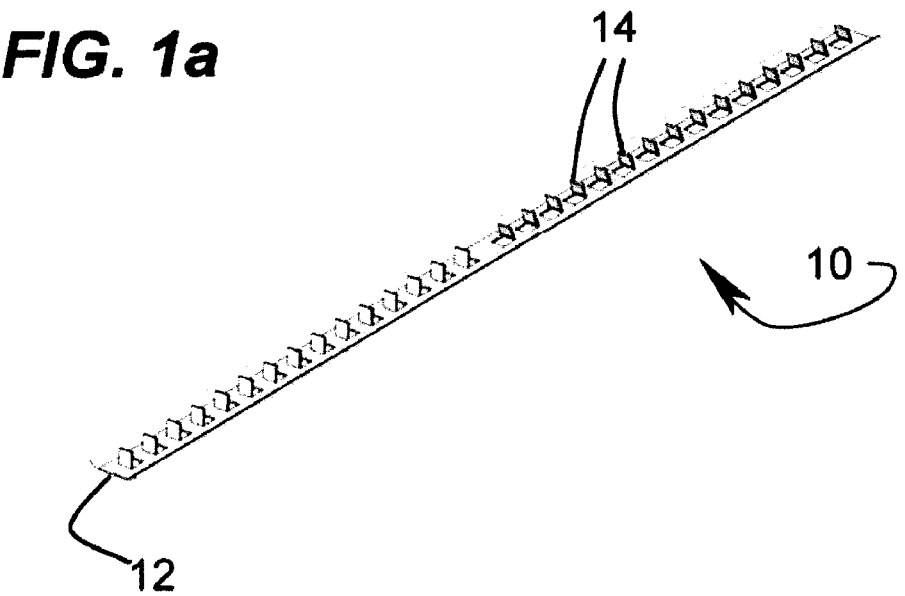
FIGS. 1a-c Isometric, top, and end views, respectively, of the invention.
Figure 1B:
Figure 1C:
Figure 2:
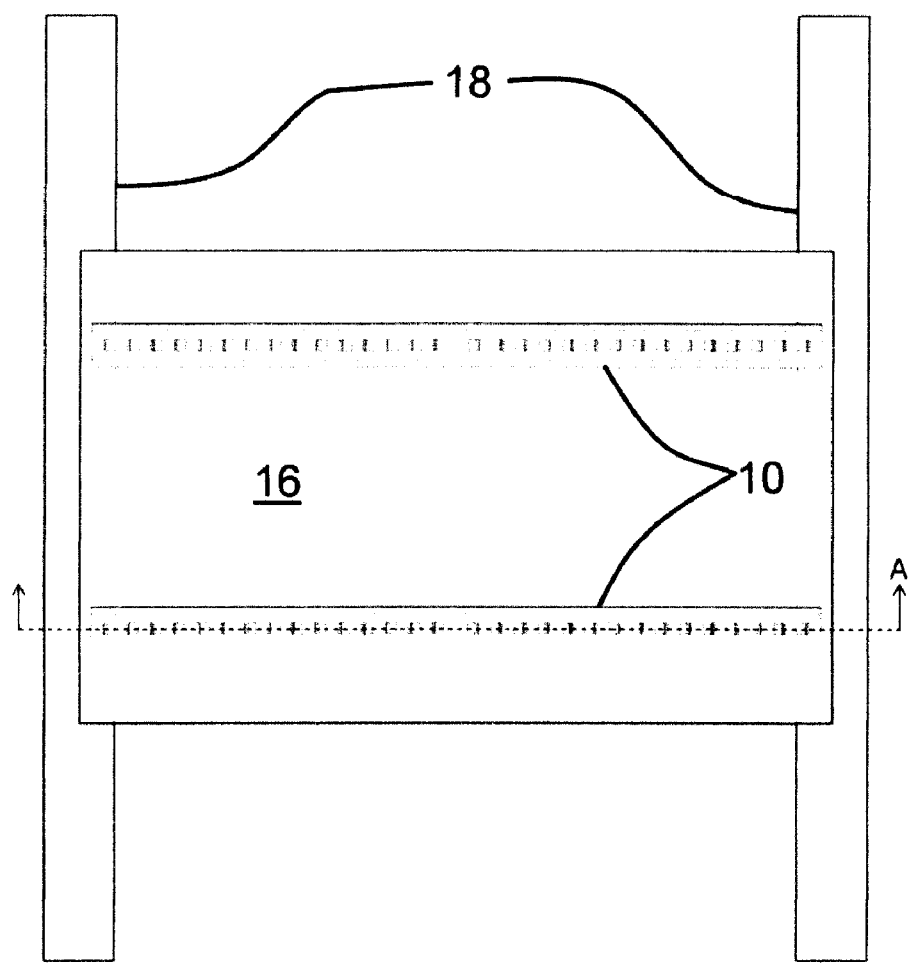
FIG. 2 Bottom view of the invention embedded in a tile.

A reinforcement element (10) for a concrete tile (16) is formed of a flat and rectangular element (12) that is placed on the underside surface a tile (16). The reinforcing element (12) has a plurality of angled scales (14) which are deeply embedded into the concrete of the tile (16) so as to provide increased adherence to the tile (16). The reinforcement element (12) is made of a strong material such as galvanized steel, or such metal treated against corrosion, or non-corroding metal or any material suitable for the task such as polymers and existing or yet to be invented composite material. The main purpose here being to provide a way to prevent the tile (10) from being overly deformed to the point of breaking. With this reinforcement element (12), no mesh or rebars are required.

The scales (14) are angled in such a way that half of the scales (14) are slanted in one direction and the other half of the scales (14) are slanted in the opposite direction, and all the scales (14) are slanted towards the center of the reinforcement element (12) so that once the concrete is cured, it is impossible for the reinforcement element (10) to slide out. Also, the opposing slant of the scales (14) creates a compressive force which keeps the tile (16) from bending. The tile (16) can be laid on a sub-structure (18) such as wooden beam or studs.

To further prevent the bending of the tile, the reinforcement element (10) has a pair of parallel folds (24) running along both sides of its length.

In a preferred embodiment, the reinforced concrete tile (16) or slab of the invention is generally rectangular, and therefore having a length, a width and a thickness associated therewith. However it will be appreciated that different shapes such a square, hexagonal or triangular shapes for example would be encompassed provided the reinforced tile possess some of the strength characteristics described below. The tile (16) or slab is intended to be structural, meaning that it is capable of bearing a load. It can be disposed on structural supports as shown, for example, in FIG. 3. The tile (16) or slab has a top side (load bearing surface) and a bottom side.

Figure 3:
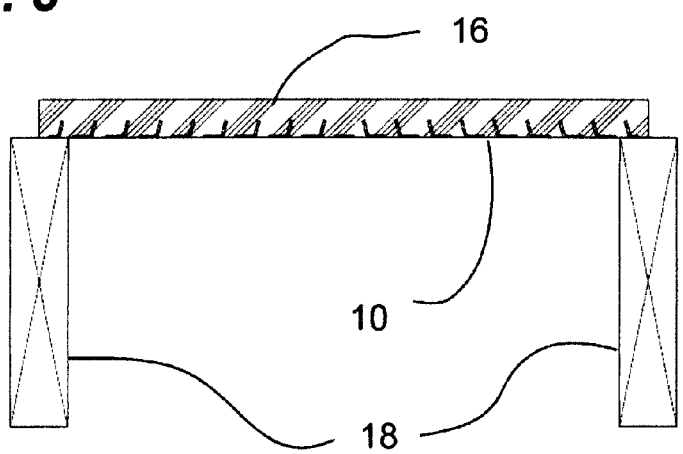
FIG. 3 Side cutaway view along line AA of the invention embedded in a tile installed on a sub-structure.
Figure 4:
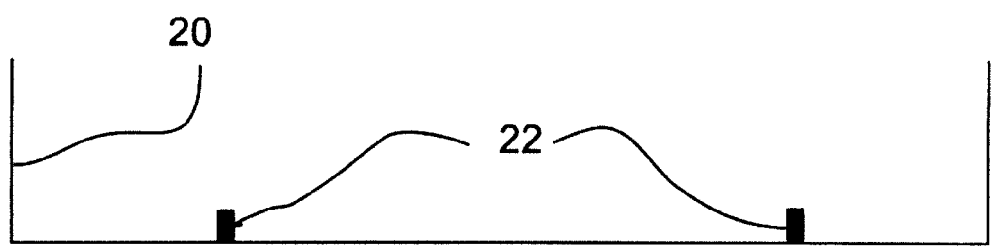
FIG. 4 Cutaway side view of a mold with pegs.
Figure 5:
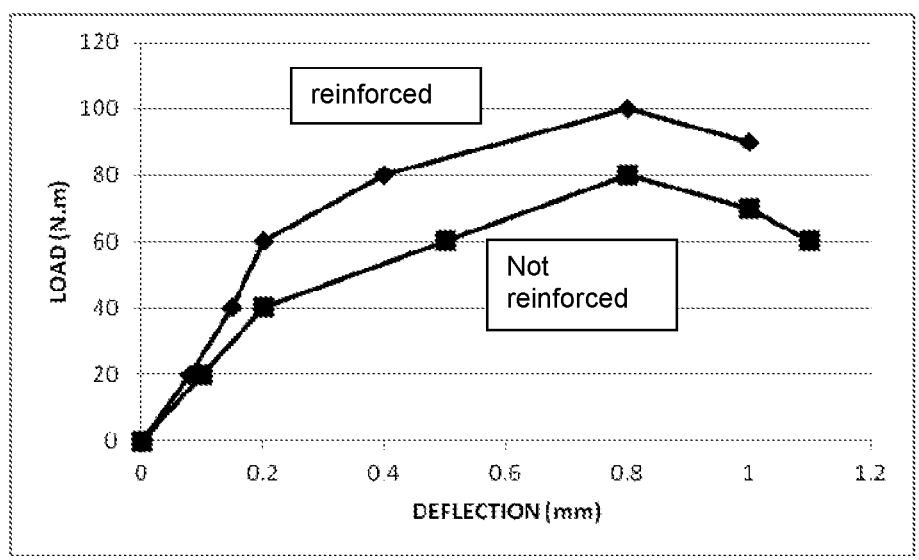
FIG. 5 (PRIOR ART) is a graph of a deflection curve for concrete tiles.

One way to study the load stress response of concrete tiles or slabs is by applying increasing flexural loads on the tile, the opposite extremities of which are resting on supports in a manner similar to the arrangement shown in FIG. 3, and measuring its deflection along the horizontal axis perpendicular to the surface of the tile. In the prior art this is referred to as a deflection curve or load-deflection curve. A typical deflection curve for concrete tiles or slab is shown in FIG. 5 (prior art). As the force (the load) applied to a tile is increased the deflection also increases. Linearly at first (in the elastic response range) and then at a rate that diminishes after cracks in the tile start to appear. After appearance of the cracks the application of additional force results in further deflection but at a different rate relative to the load increase.

Figure 6:
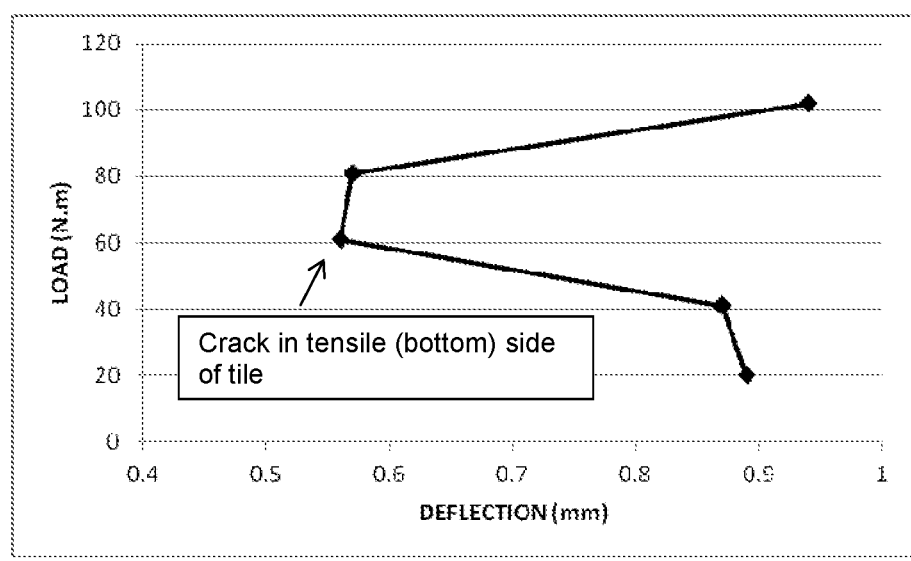
FIG. 6 is a graph of a deflection curve of a dry cast tile of the present invention.
Figure 7:
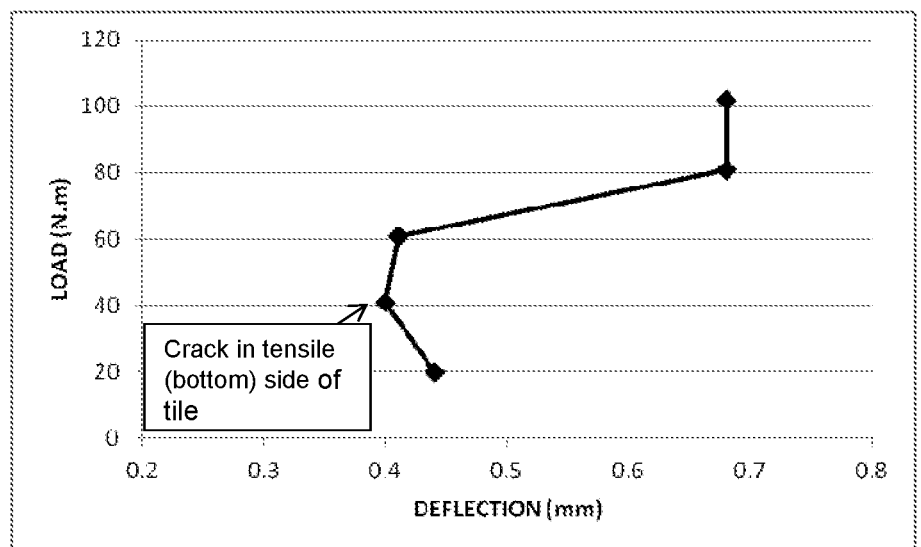
FIG. 7 is a graph of a deflection curve of a wet cast tile of the present invention.

It has been surprisingly found that the reinforced tile of the present invention exhibits an unexpected deflection curve pattern in response to loads. It has been found that, without wishing to be bound by theory, the reinforcements (or reinforcement elements or inserts) (12) of the present invention provide a compensating force in response to loads resulting in increased stress resistance. The load-deflection curves obtained reinforced tiles of the invention exhibit a decrease in the deflection as the load is increased for at least a range of increasing loads. For example, as shown in FIGS. 6 and 7 for a wet cast (dimensions of tile: Thickness 1¼", width 16", length 20") and dry cast (dimensions of tile: Thickness 1", width 10", length 16") tile respectively, as the load is initially increased there is a reduction in deflection prior to appearance of cracks. The load at which cracks start to appear is referred to as the yield load.

Thus in one embodiment of the invention the reinforcements, or reinforcing inserts (12), are imbedded in the concrete in proximity of the bottom surface of the tile. The scales (14) of the reinforcing inserts (12) extend upwardly towards the top side of the tile and span between about 10 and 80% and preferably between 25 and 50% of the thickness of the slab at a density (number of scales per length of tile) of about 1 scale per 10% of length of the tile to 1 scale per 1% of the length of the tile and more preferably between about 2% and 7% of length of the tile.

By way of example, if the thickness of the tile is 1¼ (1.25) inch then the scales (14) would expend from the bottom of the tile to a height of between 0.125 and 1 inch and more preferably between 0.3125 and 0.625 inch. And for a length of the tile of 16" there would be between about 1 scale per 0.16 linear inch to 1 scale per 1.6 linear inch and preferably between 1 scale per 0.32 linear inch and 1 scale per 1.4 inch.

As mentioned above the scales (14) are preferably at an angle relative to the length of the insert. The range of permissible angles for the scales comprises angles that would result in the height of the scales, measured perpendicularly from the bottom surface to fall within the aforementioned ranges.

The number of scales (14) in the reinforcing inserts (12) may also dependent on the design of the insert. For example, the insert (12) may be an elongated metal sheet (galvanized steel for example) in which the scales (14) are formed by punching openings at intervals along the insert (12). In such a case the number of scales (14) will in part be dictated by their height and required density.

The width of the scales is between about 1% to 25% of the width of the tile i.e. for a tile with a width of 10" the scales would have a width of about 0.1 to 2.5 inch.

It was observed that when the pattern of load-deflection curve of FIG. 6 or 7 is observed in a reinforced tile it exhibits an increased strength, as measured by the yield load of an equivalent unreinforced tile of at least 20%, preferably at least 50% and more preferably at least 100%.

For example it was observed that outside the structural characteristics described herein for the reinforced tile (16), the tile may not exhibit the unexpected reinforcement characteristics of the invention. For example, when two reinforcement inserts (12) in a 16" wide tile made of a wet cast concrete of about 35 MPa, it was found that the tile did exhibit the desired load deflection curve pattern compatible with an enhanced structural of support.

It has been found that the optimal spacing between the reinforcing inserts (12) for a rectangular tile made of concrete having a compression strength of between about 20 and 70 Mega Pascal (MPa) is between about 20 and 60% of the width of the tile for a tile about 1 to 2 inches thick. More preferably the spacing is between 25% and 50% of the width of the tile with any of the inserts (12) positioned preferably no more than about 30-40% of the width from an edge of the tile. It will be appreciated however that the optimum distances between the reinforcement inserts (12) may depend on the shape of the tile and can be determined by obtaining a load-deflection curve whereby tiles exhibiting the pattern of FIG. 5 or 6 are considered reinforced.

The reinforced tile of the invention enables the thickness of the tile to be reduced by at least 25% for a given compression strength of concrete and still provide an equivalent structural support compared to the unreinforced tile.

The reinforced tiles of the invention also provide a buffer load range in which the deflection does not increase with increasing loads as can be seen in FIG. 6 or 7. This buffer load range advantageously prevents a tile from undergoing further conformation changes as load is increased even after cracks start to appear up to a certain load.

In another aspect of the invention there is also provided a method for making a reinforced concrete tile (16) or slab comprising providing a mold for shaping the tile having a top and bottom surface; positioning in the mold two or more reinforcing inserts (12) to be imbedded in the concrete tile in proximity to the bottom surface, the two or more reinforcing inserts being of elongated shape and comprising a plurality of scales (14) distributed along the length and extending upwardly from the bottom surface; pouring unset concrete in the mold; permitting the concrete to set; and testing the tile to determine a strength of the tile. In one aspect the tile exhibit a yield load at least 20% greater than the unreinforced tile, preferably about at least 50% greater. In another aspect the yield load is about 100% greater.

The step of determining the strength may comprise obtaining a load-deflection curve and a tile is determined to be reinforced if the curve exhibits a reduction in deflection with increasing load for at least a range of loads smaller than the yield load.

Typically, the reinforcement element (12) is laid first at the bottom of a mold (20) and a dry mix is poured on top of it. Simple pegs (22) can act as positioning means for the reinforcement element (12). As many as 4 pegs per reinforcement elements (12) can be put. More than one reinforcement element (12) can be placed inside the mold (20). When the cement mix has sufficiently hardened, the tile (16) can be removed from the reusable mold (20). For a liquid mix (wet cast), typically, the reinforcement element are put on top, after the concrete has been poured in the reusable mold.

EXAMPLE

A load-deflection curve for a 10"×16" tile with a thickness of 1 inch produced by a dry cast technique and having a compression strength of between 45 and 60 MPa and comprising 2 reinforcement inserts was obtained using a constant rate extension dynamometer. Diameter of loading disc: 3 inches. Diameter of bag drop: 9.5 inches. Impact located in middle of tile. Weight of bag drop: 13.6 Kg. Speed of displacement for deflection: 5 mm/min. Results are shown in FIG. 6.

A load-deflection curve for a 16"×20" tile with a thickness of 1¼ inch produced by a wet cast technique and having a compression strength of between 30 and 45 MPa and comprising 3 reinforcement inserts was obtained using a constant rate extension dynamometer. Diameter of loading disc: 3 inches. Diameter of bag drop: 9.5 inches. Impact located in middle of tile. Weight of bag drop: 13.6 Kg. Speed of displacement for deflection: 5 mm/min. Results are shown in FIG. 7.

As to a further discussion of the manner of usage and operation of the present invention, the same should be apparent from the above description. Accordingly, no further discussion relating to the manner of usage and operation will be provided. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A method for manufacturing a reinforced concrete tile comprising
   a) providing a mold for shaping the concrete tile having a top and bottom surface defining a thickness;
   b) providing two or more reinforcing inserts of flat and elongated shape with a length and a width, and having top and bottom surfaces and comprising a plurality of scales, formed by punching openings in the two or more reinforcing inserts, distributed along the length, centered along the width, and extending upwardly from the top surface of the flat elongated shape, such that a portion of the reinforcing insert extends on both sides of each scale in the width direction, and wherein a first set of about half of the plurality of scales are slanted, at a predetermined angle, in a first direction towards a center of the tile and a second set of about half of the plurality of scales are slanted, at the predetermined angle, in a second direction, opposite the first direction, towards the center of the tile;

c) positioning in the mold the two or more reinforcing inserts to be imbedded in the concrete tile in proximity of the bottom surface at a predetermined position and spacing, the bottom surface of the reinforcing inserts facing the bottom surface of the concrete tile and the scales extending to a predetermined depth within the tile, d) pouring unset concrete in the mold;

e) permitting the concrete to set to a tile;

f) testing the tile to obtain a load-deflection curve and wherein, for a reinforced tile, deflection is reduced as the load is increased for at least a range of loads until a yield load is reached; and g) manufacturing reinforced tiles by repeating steps a-d using the predetermined positions and spacing for the inserts and predetermined depth and slant angle for the plurality of scales corresponding to the reinforced tile.

2. The method of claim 1 further comprising a step of determining a strength of the tile and wherein the strength, as measured by the yield load, is greater by about at least 20% when compared to an unreinforced tile.

3. The method of claim 2 wherein the yield load is greater by about at least 50%.

4. The method of claim 2 wherein the yield load is greater by about at least 100%.

5. The method of claim 1 wherein the depth is between 25 and 50% of the thickness.

6. The method of claim 1 wherein the reinforcing insert further comprises a pair of parallel folds running along both sides of the flat elongated shape, providing a generally flat middle portion and a slanted region on either edge of the reinforcing insert in the width direction.

7. A method for manufacturing a reinforced concrete tile comprising:

a) providing a mold for shaping the concrete tile having a top and bottom surface defining a thickness;

b) providing two or more reinforcing inserts of flat and elongated shape with a length and a width, and having top and bottom surfaces and comprising a plurality of scales, distributed along the length, centered along the width, and extending upwardly from the top surface of the flat elongated shape, such that a portion of the reinforcing insert extends on both sides of each scale in the width direction, and wherein a first set of about half of the plurality of scales are slanted, at a predetermined angle, in a first direction towards a center of the tile and a second set of about half of the plurality of scales are slanted, at the predetermined angle, in a second direction, opposite the first direction, towards the center of the tile;

c) positioning in the mold the two or more reinforcing inserts to be imbedded in the concrete tile in proximity of the bottom surface at a predetermined position and spacing, the bottom surface of the reinforcing inserts facing the bottom surface of the concrete tile and the scales extending to a predetermined depth within the tile, d) pouring unset concrete in the mold;

e) permitting the concrete to set to a tile;

f) testing the tile to obtain a load-deflection curve and wherein, for a reinforced tile, deflection is reduced as the load is increased for at least a range of loads until a yield load is reached; and g) manufacturing reinforced tiles by repeating steps a-d using the predetermined positions and spacing for the inserts and predetermined depth and slant angle for the plurality of scales corresponding to the reinforced tile.

* * * * *